United States Patent
Tsuji et al.

(10) Patent No.: US 8,814,801 B2
(45) Date of Patent: Aug. 26, 2014

(54) VESSEL WALL MONITORING APPARATUS

(75) Inventors: Toshio Tsuji, Hiroshima (JP); Masao Yoshizumi, Hiroshima (JP); Masashi Kawamoto, Hiroshima (JP); Yukihito Higashi, Hiroshima (JP); Noboru Saeki, Hiroshima (JP); Ryuji Nakamura, Hiroshima (JP); Abdugheni Kutluk, Hiroshima (JP); Akinobu Kohno, Hiroshima (JP); Tetsuya Horiuchi, Hiroshima (JP); Teiji Ukawa, Tokyo (JP)

(73) Assignees: Nihon Kohden Corporation, Tokyo (JP); Hiroshima University, Hiroshima (JP)

(*) Notice: Subject to any disclaimer, the term of this patent is extended or adjusted under 35 U.S.C. 154(b) by 811 days.

(21) Appl. No.: 12/953,743

(22) Filed: Nov. 24, 2010

(65) Prior Publication Data

US 2011/0125034 A1 May 26, 2011

(30) Foreign Application Priority Data

Nov. 26, 2009 (JP) ................................. 2009-268901

(51) Int. Cl.
*A61B 5/02* (2006.01)
*A61B 5/00* (2006.01)

(52) U.S. Cl.
USPC ........................................................ 600/485

(58) Field of Classification Search
USPC .................. 600/301, 488, 481–486, 490, 504
See application file for complete search history.

(56) References Cited

U.S. PATENT DOCUMENTS

| 6,511,436 B1* | 1/2003 | Asmar .......................... 600/500 |
| 2006/0173366 A1* | 8/2006 | Hasegawa ...................... 600/485 |
| 2006/0211942 A1* | 9/2006 | Hoctor et al. .................. 600/438 |

FOREIGN PATENT DOCUMENTS

| JP | 2006-129958 | * | 5/2006 | ............... A61B 5/02 |
| JP | 2006-129958 A | | 5/2006 | |
| JP | 2008-061910 | * | 3/2008 | ............... A61B 5/02 |
| JP | 2008-61910 A | | 3/2008 | |

OTHER PUBLICATIONS

Monitoring of Vascular Conditions Using Plethysmogram, The Journal of the Society of Instrument and Control Engineering, vol. 40, No. 12, p. 1236-1242, 2004.
Biomechanics, P73, 2000, Corona Publishing Co., Ltd.

* cited by examiner

*Primary Examiner* — Jacqueline Cheng
*Assistant Examiner* — Puya Agahi
(74) *Attorney, Agent, or Firm* — Kenealy Vaidya LLP

(57) ABSTRACT

A vessel wall monitoring apparatus includes: a first detecting unit which detects vessel diameter information based on first biological information obtained from a subject; a first producing unit which differentiates the vessel diameter information detected by the first detecting unit, to produce a vessel diameter function; a second detecting unit which detects blood pressure based on second biological information obtained from the subject; a second producing unit which performs a logarithmic operation on the blood pressure detected by the second detecting unit, to produce a logarithmic blood pressure function; and an outputting unit which produces an impedance model expression by using the vessel diameter function, the logarithmic blood pressure function, and mechanical characteristic values including a stiffness, viscosity, and inertia, and which calculates and outputs at least one of the stiffness, the viscosity, and the inertia based on the impedance model expression.

14 Claims, 16 Drawing Sheets

VESSEL WALL MONITORING APPARATUS

BACKGROUND OF THE INVENTION

The present invention relates to a vessel wall monitoring apparatus which, in the case where a vessel wall is modeled in a mechanical impedance model, are used for monitoring mechanical characteristics of the vessel wall, such as the viscosity, the stiffness, and the inertia.

A vessel plays an important role in carrying oxygen, nutrients, and the like to the whole body in human life support, and changes its state such as dilation and contraction to adjust the blood volume or the like. Such state changes of a vessel are roughly classified into a functional change and an organic change.

A functional change means that peripheral circulation of the human body adjusts dilation and contraction in accordance with a stimulus to the human body. The functional change is produced by a phenomenon that a sympathetic nerve of the autonomic nervous system reacts to a stimulus from the outside of the human body, and the reaction of sympathetic nerve causes a vessel to contract and relax.

During surgery on the human body, therefore, the peripheral circulation is susceptible. In order to know a state change of the peripheral circulation, it is important to monitor mechanical characteristics of a vessel.

By contrast, an organic change means that collagen in the artery wall is metamorphosed and hardened with age or the like and elastic fibers are reduced. In the organic change, organic degeneration of the hardness of the vessel wall is known as a symptom which is called arteriosclerosis.

As described above, in vessel disease, it is highly needed to monitor mechanical characteristics of a vessel wall ranging from short-term monitoring of a patient to chronic disease such as arteriosclerosis, thereby knowing the state of the vessel wall.

In response to such a request, a measuring apparatus in which a vessel wall is modeled in a mechanical impedance model, and factors of the vessel wall such as the inertia, the viscosity, and the stiffness are output has been proposed (see Non-patent Reference 1 and Patent Reference 1). According to the apparatus, based on an electrocardiogram and blood pressure of the patient, and a plethysmogram of blood flowing through a vessel, it is possible to output the above-described mechanical characteristics of the vessel wall, i.e., the inertia, the viscosity, and the stiffness. When the apparatus is used on a patient under surgery, mechanical characteristics of a vessel wall of the patient such as the inertia, the viscosity, and the stiffness can be monitored and the state of the vessel wall of the patient can be known.

It has been experimentally ascertained that the relationship between the blood pressure and the vessel diameter exhibits non-linearity. By contrast, in the apparatus disclosed in Non-patent Reference 1 above, it is assumed that the relationship exhibits linearity (see Exp. 1 of Non-patent Reference 1), and the position is taken that the dependence on the blood pressure itself is information. However, in order to know the degree of tension of the vessel wall due to autonomic nervous activity, and an organic change of the vessel wall due to arteriosclerosis, the high blood pressure dependency with respect to an estimated stiffness value is problematic.

With respect to the problem of the blood pressure dependency, Hayashi et al experimentally show that, when logarithm is applied to the term of the intravascular pressure, the relationship between the human vessel diameter and the intravascular pressure can be linearized, and propose the stiffness parameter, $\beta$ (hereinafter, this parameter is indicated by $\beta_{sf}$, and the stiffness obtained in the invention is indicated by $\beta$) as an evaluation index of the vessel elasticity (see Non-patent Reference 2).

In the index, however, only the stiffness of a vessel wall is considered, and only the maximal and minimal blood pressures and the maximum and minimum vessel diameters are used in the estimation. Therefore, it is difficult to evaluate in detail vessel mechanical characteristics. Moreover, also an apparatus which estimates the stiffness and viscosity of a vessel wall based on the maximal and minimal blood pressures and the maximum and minimum vessel diameters is known (see Patent Reference 1).

[Patent Reference 1] JP-A-2006-129958
[Patent Reference 2] JP-A-2008-61910
[Non-patent Reference 1] Monitoring of Vascular Conditions Using Plethysmogram, Akira SAKANE, Toshio TSUJI, Yoshiyuki TANAKA, Noboru SAEKI, and Masashi KAWAMOTO, The journal of the Society of Instrument and Control Engineering, Vol. 40, No. 12, pp. 1236-1242, 2004
[Non-patent Reference 2] Kosaburo HAYASHI, Biomechanics, P73, 2000, Corona Publishing Co., Ltd

SUMMARY

It is therefore an object of the invention to provide a vessel wall monitoring apparatus which has no blood pressure dependency, and which, even when the blood pressure of the subject is changed, can faithfully estimate mechanical characteristics of a vessel.

In order to achieve the object, according to the invention, there is provided a vessel wall monitoring apparatus comprising: a first detecting unit which detects vessel diameter information based on first biological information obtained from a subject; a first producing unit which differentiates the vessel diameter information detected by the first detecting unit, to produce a vessel diameter function; a second detecting unit which detects blood pressure based on second biological information obtained from the subject; a second producing unit which performs a logarithmic operation on the blood pressure detected by the second detecting unit, to produce a logarithmic blood pressure function; and an outputting unit which produces an impedance model expression by using the vessel diameter function, the logarithmic blood pressure function, and mechanical characteristic values including a stiffness, viscosity, and inertia, and which calculates and outputs at least one of the stiffness, the viscosity, and the inertia based on the impedance model expression.

The first detecting unit may detect the vessel diameter information based on the first biological information obtained by an ultrasonic diagnostic apparatus using an ultrasonic echo.

The vessel diameter information may include a plethysmogram, and the first detecting unit may detect the plethysmogram based on the first biological information obtained by a photoelectric sensor or a strain gauge.

The first producing unit may use the vessel diameter information detected by the first detecting unit based on the first biological information obtained at a reference appearance timing and a next reference appearance timing of a blood pressure waveform, and the second producing unit may use the blood pressure detected by the second detecting unit based on the second biological information obtained at the reference appearance timing and the next reference appearance timing of the blood pressure waveform. Each of the reference appearance timing and the next reference appearance timing may be obtained from an inflection point of the blood pressure waveform.

The first producing unit may use the vessel diameter information detected by the first detecting unit based on the second biological information obtained at a reference appearance timing and a next reference appearance timing of a blood pressure waveform, and the second producing unit may use the blood pressure detected by the second detecting unit based on the second biological information obtained at the reference appearance timing and the next reference appearance timing of the blood pressure waveform. Each of the reference appearance timing and the next reference appearance timing may be obtained from an R-wave of an electrocardiogram.

The logarithmic blood pressure function may include $dP_b(t)=\ln(P_b(t))-\ln(P_b(t_0))$, and the vessel diameter function may include: $\epsilon(t)=(r(t)-r(t_0))/r(t_0)$; $\epsilon'(t)$ which is a first derivative of $\epsilon(t)$; and $\epsilon''(t)$ which is a second derivative of $\epsilon(t)$, where $t_0$ indicates the reference appearance timing, t indicates a time period from the reference appearance timing to the next reference appearance timing, $P_b(t)$ indicates a blood pressure value at t, and r(t) indicates a vessel diameter at t. The impedance model expression may include $dP_b(t)=\ln(P_b(t))-\ln(P_b(t_0))=\beta\epsilon(t)+\eta\epsilon'(t)+\mu\epsilon''(t)$, where $\beta$ indicates the stiffness, $\eta$ indicates the viscosity, and $\mu$ indicates the inertia, on which a recurrent calculation is performed to output the at least one of the stiffness, the viscosity, and the inertia.

The logarithmic blood pressure function may include $dP_b(t)=\ln(P_b(t))-\ln(P_b(t_0))$, and the vessel diameter function may include: $dP_1(t)=(P_1(t)-P_1(t_0))$; $dP_1'(t)$ which is a first derivative of $P_1(t)$; and $dP_1''(t)$ which is a second derivative of $P_1(t)$, where $t_0$ indicates the reference appearance timing, t indicates a time period from the reference appearance timing to the next reference appearance timing, $P_b(t)$ indicates a blood pressure value at t, and $P_1(t)$ indicates a plethysmogram at t. The impedance model expression may include $dP_b(t)=\ln(P_b(t))-\ln(P_b(t_0))=\beta dP_1(t)+\eta dP_1'(t)+\mu dP_1''(t)$, where $\beta$ indicates the stiffness, $\eta$ indicates the viscosity, and $\mu$ indicates the inertia, on which a recurrent calculation is performed to output the at least one of the stiffness, the viscosity, and the inertia.

The outputting unit may detect a time difference $\tau$ between an appearance timing of the inflection point in $dP_b(t)$ and an appearance timing of the inflection point in $\epsilon(t)$, and the outputting unit may correct $dP_b(t)$ to $dP_b(t-\tau)$ and correct $dP_b(t_0)$ to $dP_b(t_0-\tau)$.

The outputting unit may calculate the stiffness and the viscosity and calculates and output a ratio of the stiffness and the viscosity.

DETAILED DESCRIPTION OF EMBODIMENTS

Figure 1:
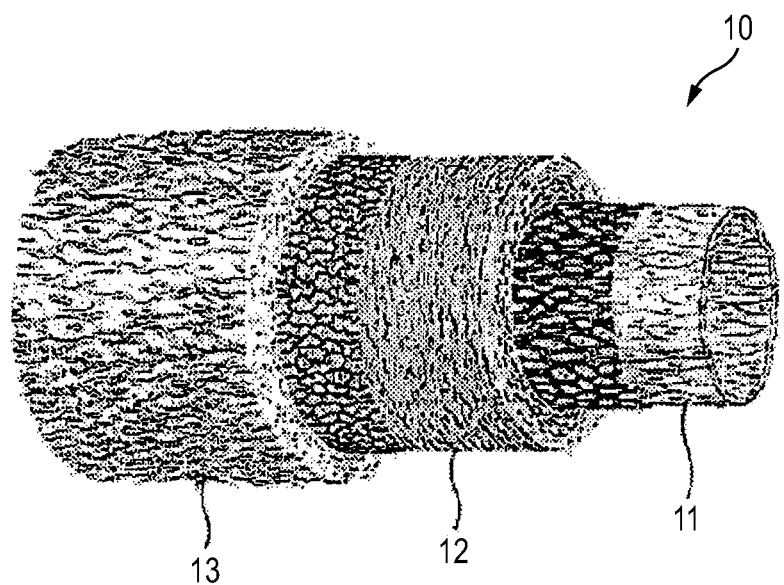
FIG. 1 is a diagram showing the structure of a human vessel.

Hereinafter, an embodiment of the vessel wall monitoring apparatus and a computer-readable recording medium on which a vessel wall monitoring program is recorded, of the invention will be described with reference to the accompanying drawings. In figures, identical components are denoted by the same reference numerals, and duplicate description will be omitted.

An embodiment of the invention will be described with reference to the figures. As described below, the vessel wall monitoring apparatus of the embodiment which, in the case where an artery vessel wall (in the specification, referred to merely as "vessel wall") is modeled in a mechanical impedance model based on an electrocardiogram, blood pressure, and plethysmogram of the patient, outputs mechanical characteristic values of the stiffness (elasticity), viscosity, and inertia of the vessel wall. For the sake of convenience in description, hereinafter, the modeling, the plethysmogram, and the method of calculating the mechanical characteristic values will be sequentially described, and thereafter the configuration of the vessel wall monitoring apparatus of the embodiment will be described.

(Modeling of Vessel Wall)

As shown in FIG. 1, a vessel wall 10 of a human body is configured by three layers of a tunica intima 11, a tunica media 12, and a tunica adventitia 13. Each of the layers includes a specific component.

The tunica adventitia 13 includes factors which affect the artery stiffness and the compliance, such as combination tissue, elastin, and collagen, and also a vasa vasorum through which nutrients are supplied to the vessel wall of the large artery.

In the tunica intima 11, there exists a vascular endothelium which produces an endothelium-derived vasoactive substance such as nitrogen monoxide and the EDHF (endothelium-derived hyperpolarizing factor).

The tunica media 12 includes smooth muscle, elastin and collagen. The smooth muscle plays a function of, when stimulated by a sympathetic nerve or a hormone, contracting to reduce the blood flow amount.

Therefore, the vessel wall 10 is caused to contract or relax by the function of the smooth muscle included in the tunica media 12. In the embodiment, as means for quantifying the degree of contraction or relaxation of the vessel wall 10, therefore, the modeling of the vessel wall 10 in a mechanical impedance model is performed.

Figure 2:
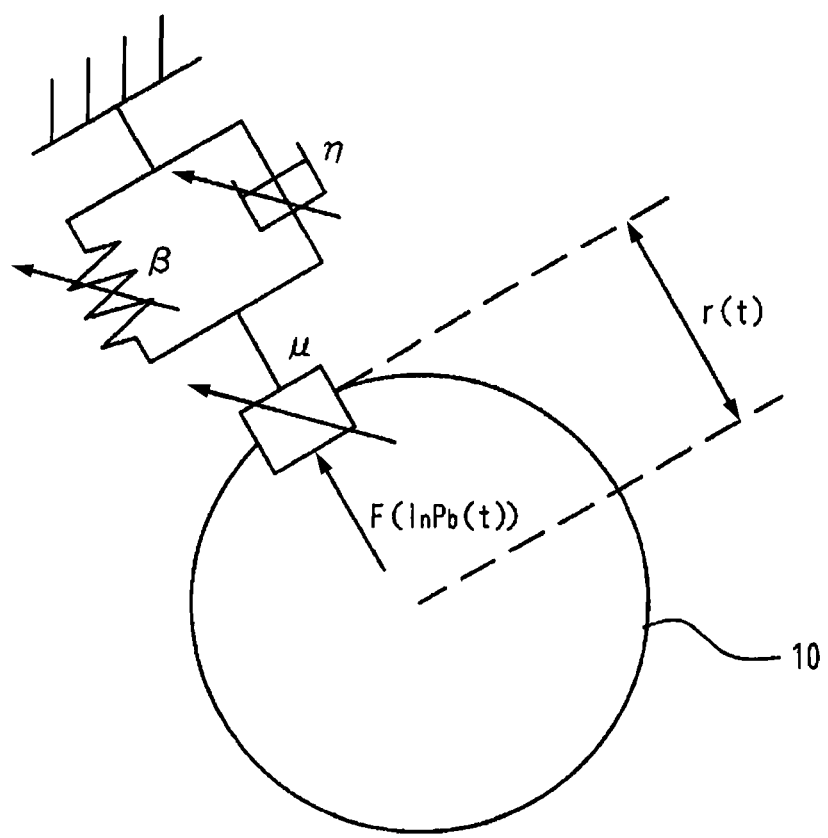
FIG. 2 is a view showing a vessel mechanical model.

FIG. 2 is a view showing a mechanical impedance model of the vessel wall 10. In the figure, $F(\ln Pb(t))$ indicates a force which is applied to the vessel wall by the blood pressure. In the embodiment, the mechanical characteristic values of $\beta$ (stiffness), $\eta$ (viscosity), and $\mu$ (inertia) in the mechanical impedance model shown in FIG. 2 are deemed to be in linear relationship with the logarithm of the blood pressure as shown in (Exp. 1), thereby realizing suppression of the blood pressure dependency.

$$dP_b(t) = \beta\epsilon(t) + \eta\epsilon'(t) + \mu\epsilon''(t)$$

$$dP_b(t) = \ln(P_b(t)) - \ln(P_b(t_0)),$$

$$\epsilon(t) = (r(t) - r(t_0))/r(t_0), \quad \text{(Exp. 1)}$$

where $t_0$: reference appearance timing, t: time period from the reference appearance timing to the next reference appearance timing, $P_b(t)$: blood pressure, $P_b(t_0)$: blood pressure at the reference appearance timing, $r(t)$: vessel diameter, $r(t_0)$: vessel diameter at the reference appearance timing, $\epsilon(t)$: strain $\epsilon'(t)$: first derivative of $\epsilon(t)$, and $\epsilon''(t)$: second derivative of $\epsilon(t)$.

Non-patent Reference 1 describes that inclusion of an inertia term in a model expression is useful for enhancing the estimation accuracy. However, the inertia $\mu$ in a vessel wall is very small, and practically there is a case where, even when vessel mechanical characteristics are expressed by using only the stiffness $\beta$ and the viscosity $\mu$, any practical problem does not arise. In the embodiment, the model expression is effective irrespective of existence or non-existence of an inertia term.

Configuration of First Embodiment

Figure 3:
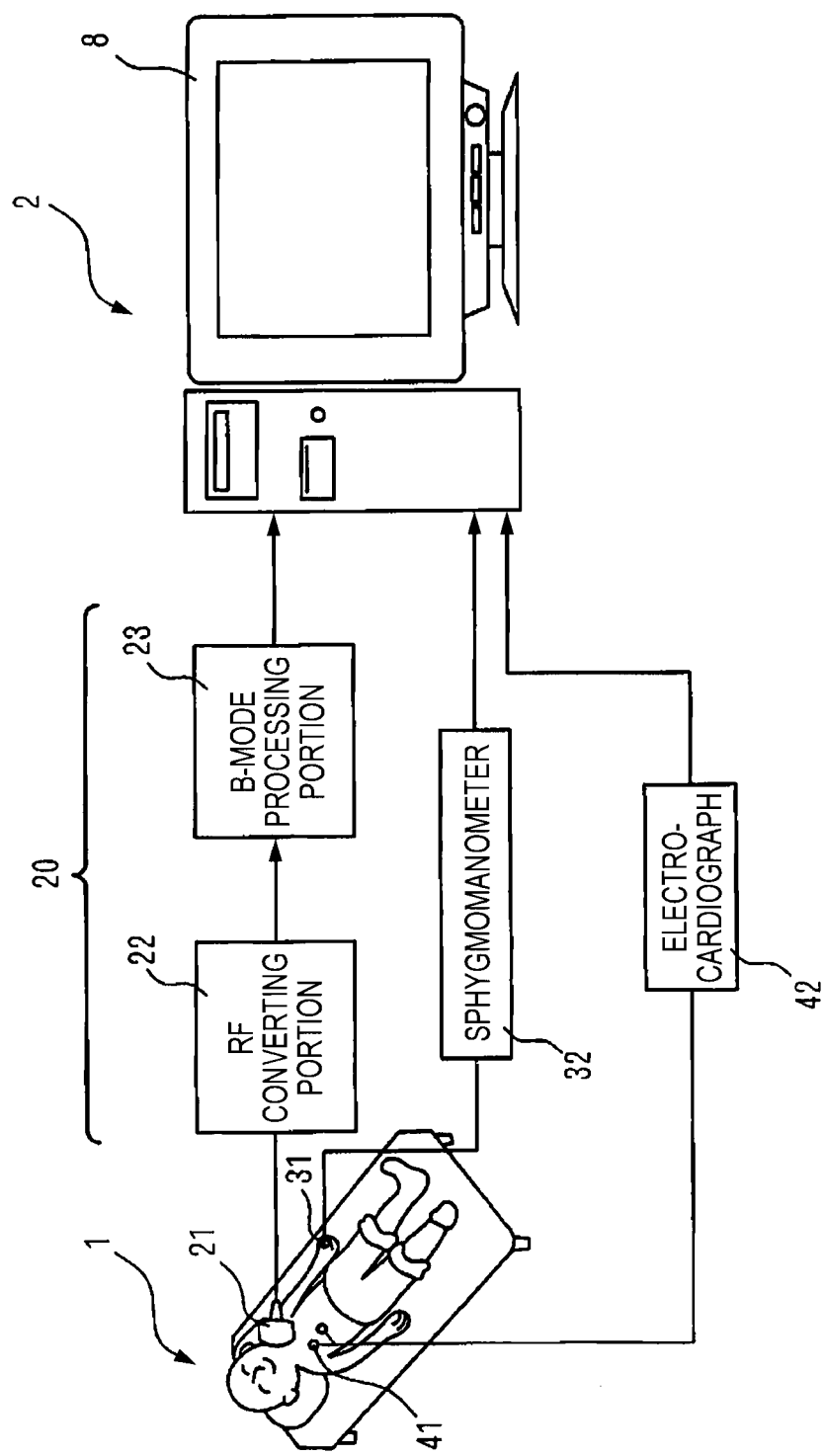
FIG. 3 is a diagram showing a first embodiment of the vessel wall monitoring apparatus of the invention.

The configuration for estimating $\beta$, $\eta$, and $\mu$ will be described with reference to (Exp. 1). In the embodiment, as shown in FIG. 3, by using an ultrasonic transducer 21, an acoustic echo of a tissue (in this case, a vessel) is obtained as first biological information from the living body of the subject 1, and converted into an electric signal. The output of the ultrasonic transducer 21 is converted in an RF converting portion 22 to an RF signal which is expressed as a complex quantity $I(t)+Q(t)$. The output of the RF converting portion 22 is sent to a B-mode processing portion 23, and converted therein to a B-mode image (gray-scale image). The image is sent to a computer system 2. The ultrasonic transducer 21, the RF converting portion 22, and the B-mode processing portion 23 constitute an ultrasonic diagnostic apparatus 20 which measures the vessel diameter $r(t)$. The blood pressure is obtained as second biological information through a catheter 31 which is inserted into a vessel, measured by a sphygmomanometer 32, and sent as a blood pressure value to the computer system 2. The blood pressure measurement may be performed by using another noninvasive measurement method such as the tonometry method.

Electrodes 41 for an electrocardiograph 42 are applied to the living body of the subject 1, and an electric signal which is obtained through the electrodes 41 is sent to the electrocardiograph 42 to be formed as an electrocardiographic signal (digital) which has undergone noise rejection and the like. The electrocardiographic signal is sent to the computer system 2.

Figure 4:
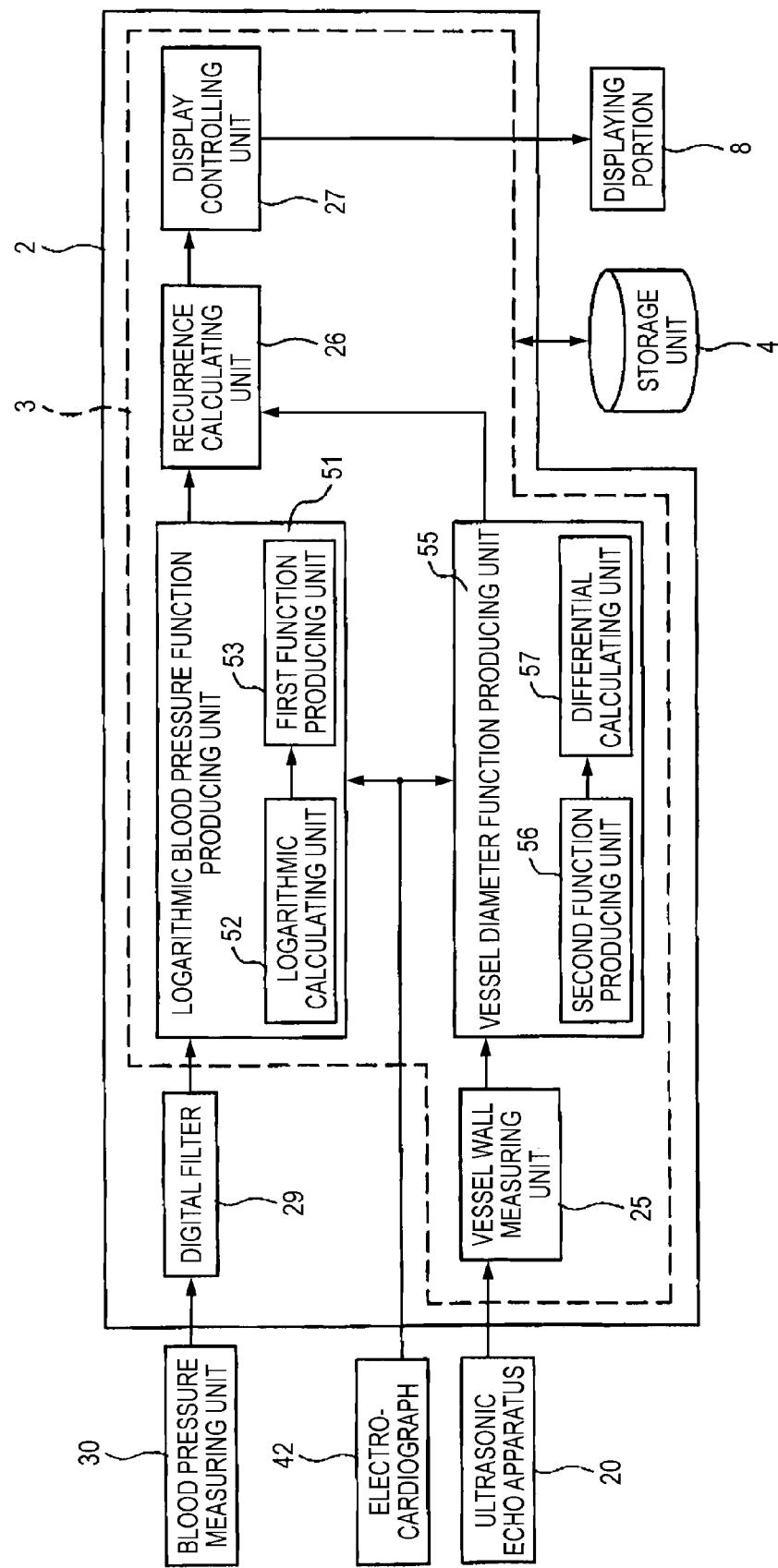
FIG. 4 is a block diagram showing the configuration of the first embodiment of the vessel wall monitoring apparatus of the invention.

FIG. 4 is a diagram showing the internal configuration of the computer system 2 of FIG. 3. A blood pressure measuring unit 30 shown in FIG. 4 is configured by, for example, the sphygmomanometer 32 in FIG. 3, and outputs a blood pressure waveform. The computer system 2 includes a computer 3 which processes biological information, and a storage unit 4 which is a computer readable recording medium. The computer 3 reads a program stored in the storage unit 4, performs a process, and stores necessary information and the like in the storage unit 4. By means of programs for vessel wall monitoring in the storage unit 4, the computer 3 realizes a vessel wall measuring unit 25, a logarithmic blood pressure function producing unit 51, a vessel diameter function producing unit 55, a regression calculating unit 26, and a display controlling unit 27.

Figure 5:
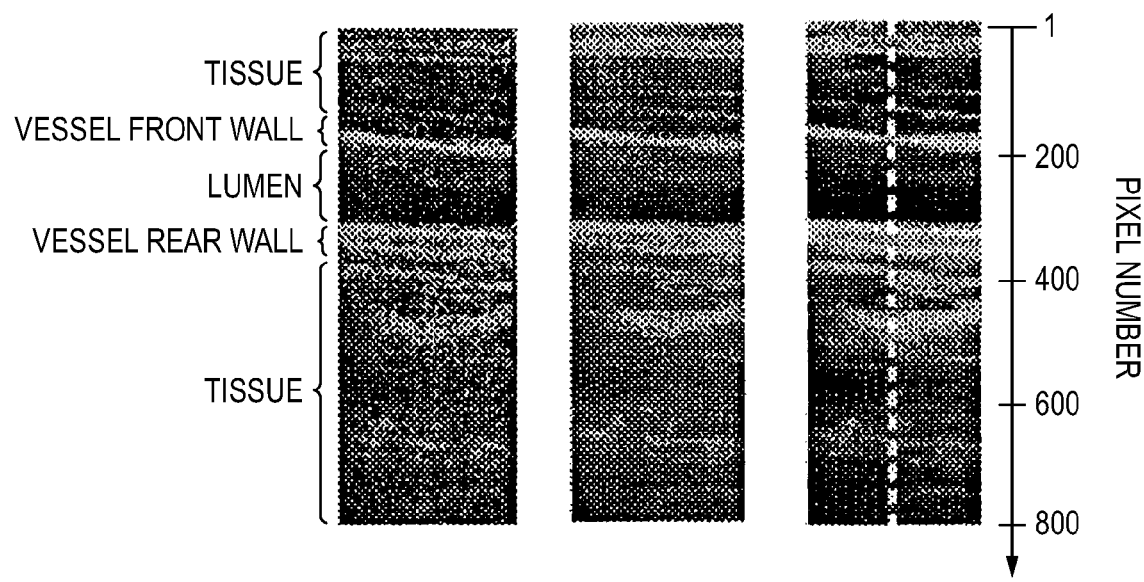
FIGS. 5A, 5B and 5C are views illustrating steps of, in the first embodiment of the vessel wall monitoring apparatus of the invention, detecting the vessel diameter from a B-mode image obtained from an ultrasonic diagnostic apparatus using an ultrasonic echo.

The vessel wall measuring unit 25 measures the vessel diameter by using the B-mode image sent from the ultrasonic diagnostic apparatus 20. An original image shown in FIG. 5A is obtained from the image sent from the ultrasonic diagnostic apparatus 20. The vessel wall measuring unit 25 performs noise reduction on the obtained original image as shown in FIG. 5B, and then gray-scale conversion as shown in FIG. 5C.

Figure 6:
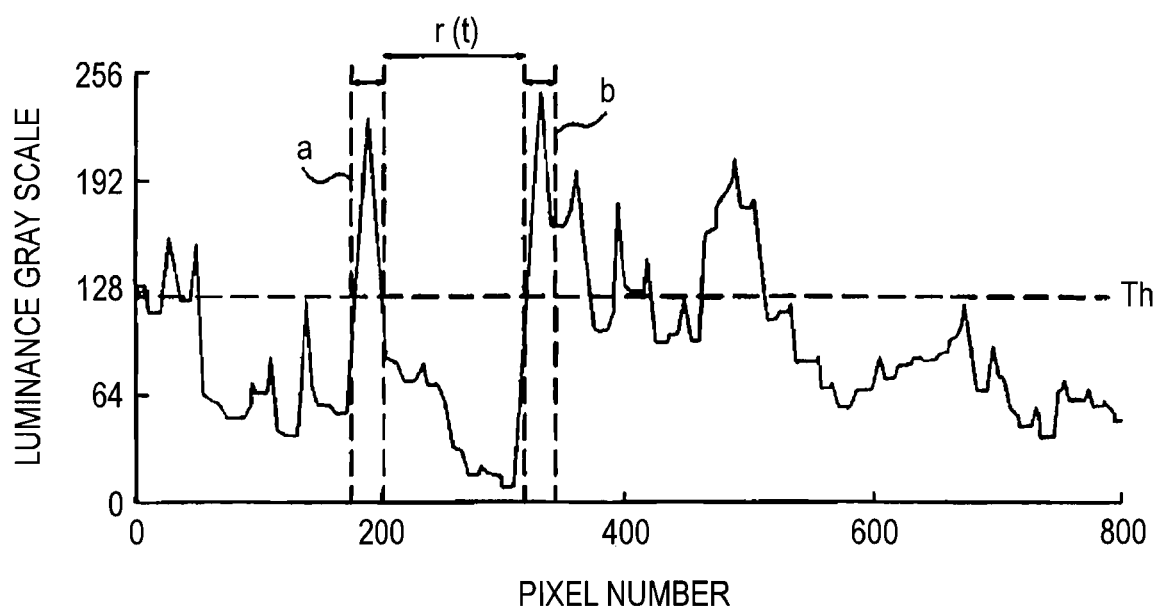
FIG. 6 is a view illustrating detection of the vessel diameter from a B-mode image obtained from an ultrasonic diagnostic apparatus using an ultrasonic echo, in the first embodiment of the vessel wall monitoring apparatus of the invention.

The one row of brightness values indicated by the dotted line shown in FIG. 5C are shown in a form in which the brightness is indicated as the ordinate, resulting in that the chart of FIG. 6 is obtained. In the figure, the distance between the vessel front wall a and the vessel rear wall b is the vessel diameter $r(t)$. The vessel wall measuring unit 25 sets a predetermined threshold Th, and detects the vessel wall to obtain the vessel diameter $r(t)$.

In the measurement of the vessel diameter, specifically, a threshold at which the vessel wall can be suitably extracted from an initial frame image, and a lumen pixel which functions as a vessel wall search center pixel are first experimentally set. Next, scanning is performed on each one [pixel] with starting from the search center pixel to search pixels in which the brightness exceeds the threshold. The searched pixels are set as vessel inner wall points. A pixel which is smaller in pixel number than the search center pixel is set as a vessel front wall a, and that which is larger in pixel number is set as a vessel rear wall b. All columns of the image are similarly processed, and the vessel front wall points and rear wall points of the rows are obtained. By using these points, approximation lines of the front and rear walls are respectively obtained, and the pixel distance between the lines is measured. In this case, the inclinations of the lines are calculated from the coordinates in the image, and the measured pixel distance is corrected.

The slope of the line on the side of the front wall is different from that on the side of the rear wall, and hence the arithmetic average of the all columns of the image is set as the vessel diameter r(t). Similar processes are performed on all frame images to obtain a vessel displacement waveform. The vessel diameter r(t) is sent to the vessel diameter function producing unit 55.

The vessel diameter function producing unit 55 includes a second function producing unit 56 and a differential calculating unit 57. The second function producing unit 56 produces strain $\epsilon(t)=(r(t)-r(t_0))/r(t_0)$, based on the vessel diameter r(t). The strain $\epsilon(t)$ is sent to the differential calculating unit 57.

The differential calculating unit 57 calculates the first derivative $\epsilon'(t)$ of $\epsilon(t)$ and the second derivative $\epsilon''(t)$ of $\epsilon(t)$, and $\epsilon(t)$, $\epsilon'(t)$, and $\epsilon''(t)$ are sent to the regression calculating unit 26.

By contrast, the blood pressure value which is output from the blood pressure measuring unit 30 is subjected to noise rejection by a digital filter 29, and then sent to the logarithmic blood pressure function producing unit 51. The logarithmic blood pressure function producing unit 51 includes a logarithmic calculating unit 52 and a first function producing unit 53.

The logarithmic calculating unit 52 produces logarithms $\ln(P_b(t))$ and $\ln(P_b(t_0))$ of the blood pressure values $P_b(t)$ and $P_b(t_0)$ which are sent from the digital filter 29, and sends the logarithms to the first function producing unit 53. The first function producing unit 53 obtains $\ln(P_b(t))$ and $\ln(P_b(t_0))$, and produces a function of $dP_b(t)=\ln(P_b(t))-\ln(P_b(t_0))$ which is a first function, and sends the function to the regression calculating unit 26.

In the logarithmic blood pressure function producing unit 51 and the vessel diameter function producing unit 55, the reference appearance timing is obtained from an inflection point of the blood pressure waveform. In the case where fetching is performed while the reference appearance timing is indicated by $t_0$, and the time period from the reference appearance timing to the next reference appearance timing is indicated by t, data are fetched at the timing of an inflection point of the blood pressure waveform, and therefore the logarithmic blood pressure function producing unit 51 and the vessel diameter function producing unit 55 can synchronously fetch data. Since the electrocardiographic signal is given from the electrocardiograph 42, alternatively, the reference appearance timing may be obtained from the R-wave of the electrocardiogram.

The regression calculating unit 26 obtains the following functions from the logarithmic blood pressure function producing unit 51 and the vessel diameter function producing unit 55, $dP_b(t)=\ln(P_b(t))-\ln(P_b(t_0))$, $\epsilon(t)$, $\epsilon'(t)$, and $\epsilon''(t)$. When the stiffness $\beta$, the viscosity $\eta$, and the inertia $\mu$ are used, while $dP_b(t)$, $\epsilon(t)$, $\epsilon'(t)$, and $\epsilon''(t)$ above are set as samples, therefore, the regression calculating unit 26 produces an impedance model expression of $dP_b(t)=\ln(P_b(t))-\ln(P_b(t_0))=\beta\epsilon(t)+\eta\epsilon'(t)+\mu\epsilon''(t)$, and the stiffness $\beta$, the viscosity $\eta$, and the inertia $\mu$ are obtained by a recurrent calculation.

Specifically, the arterial blood pressure and strain at time t for one heart beat are substituted into the impedance model expression above, and fitting based on the least squares method is performed, whereby the stiffness $\beta$, the viscosity $\eta$, and the inertia $\mu$ are estimated from continuous data for one heart beat. The output of the regression calculating unit 26 is subjected to an outputting process such as that the output is caused by the display controlling unit 27 to be displayed on a displaying portion 8.

In the measurement of a vessel viscoelastic index based on continuous data for one heart beat, the vessel displacement waveform and the blood pressure waveform must be synchronized with each other. Depending on the measurement portion, however, there is a case where the synchronization is hardly realized. Furthermore, it is necessary to consider also the measurement delay time which is inherent to the apparatus. Therefore, a method is employed in which synchronization is attained by shifting the phase of the measured blood pressure waveform and that of the blood pressure waveform estimated from the model so that their coefficients of determination are maximum, thereby estimating a vessel viscoelastic index. In the case where such an estimation is performed, the impedance model expression is expressed in the following manner.

$$dP_b(t)=\ln(P_b(t-\tau))-\ln(P_b(t_0-\tau))=\beta\epsilon(t)+\eta\epsilon'(t)+\mu\epsilon''(t)$$

Specifically, the regression calculating unit 26 may detect the time difference $\tau$ between the appearance timing of an inflection point in $dP_b(t)$ above, and that of an inflection point in $dP_b(t)$ above or $\epsilon(t)$, correct $dP_b(t)$ above to $dP_b(t-\tau)$, and correct $dP_b(t_0)$ above to $dP_b(t_0-\tau)$.

Next, a comparison between a related-art model and a log-linearization model which is realized by the embodiment, i.e., data showing an advantage of the log-linearization model will be described in the form of a plethysmogram. Here, an advantage of a model in which the viscosity term is considered, as compared with the stiffness parameter $\beta_{sf}$ is shown. In the experiment, $dP_b(t)=\ln(P_b(t))-\ln(P_b(t_0))=\beta\epsilon(t)+\eta\epsilon'(t)$ is set, and the inertia $\mu$ is not considered.

Figure 7A:
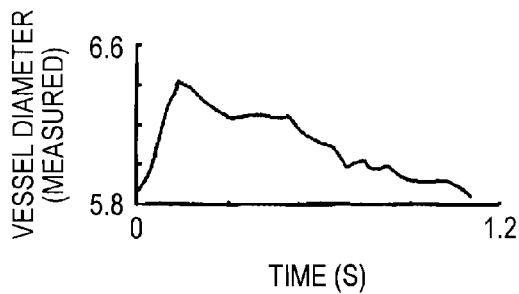
FIGS. 7A to 7F are views showing that estimated values from mechanical characteristic values obtained in the first embodiment of the vessel wall monitoring apparatus of the invention coincide with measured values.
Figure 7D:
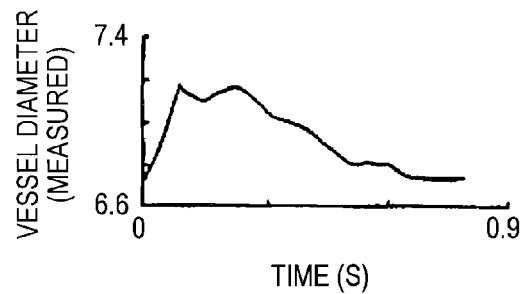
Figure 7B:
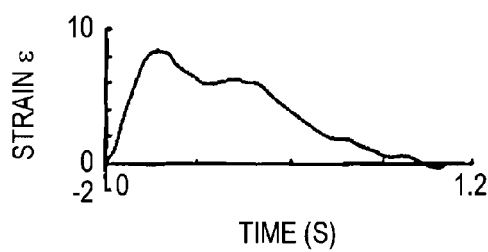
Figure 7E:
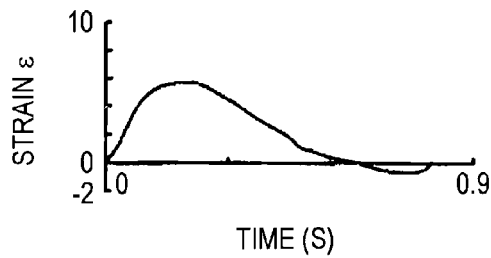
Figure 7C:
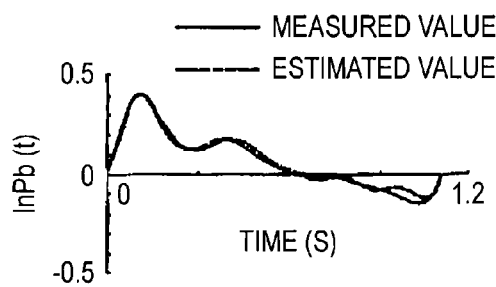
Figure 7F:
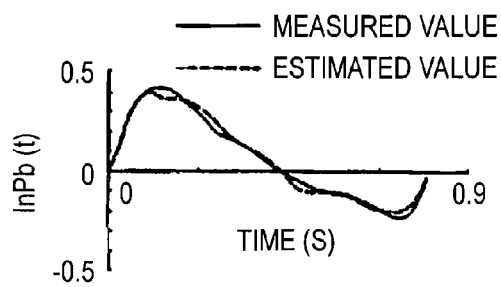

FIGS. 7A to 7F are views showing the degree of coincidence between a blood pressure which is estimated from the vessel diameter by the least squares method, and the measured blood pressure waveform. FIGS. 7A, 7B and 7C show vessel diameter waveforms for one heart beat obtained from a twentysomething subject, and FIGS. 7D, 7E and 7F show those obtained from a sixtysomething subject. FIGS. 7A and 7D show measured waveforms of the vessel diameter, and FIGS. 7B and 7E show smoothed strain c waveforms. FIGS. 7C and 7F show the blood pressure waveform $\ln(P_b(t))$ (broken line) that is estimated by a log-linearization function estimated by the above-described model expression in which $\mu$ is 0 and $\beta$ and $\eta$ are used, and the blood pressure waveform $\ln(P_b(t))$ (solid line) obtained from a measured linear logarithm function. In both the cases shown respectively in FIGS. 7C and 7F, the coefficient of determination between the measured value and the estimated value is 0.95 or more. It is seen that the values are in good coincidence.

By contrast, the stiffness parameter $\beta_{sf}$ in the related-art method is obtained by the following expression, and the terms other than the stiffness are not considered. In the following expression, $P_s$, $P_d$, $r_s$, and $r_d$ indicate the maximal blood pressure, the minimal blood pressure, the maximum vessel diameter, and the minimum vessel diameter, respectively.

$$\beta_{sf}=(\ln(P_s/P_d))/((r_s-r_d)/r_d)$$

Figure 8:
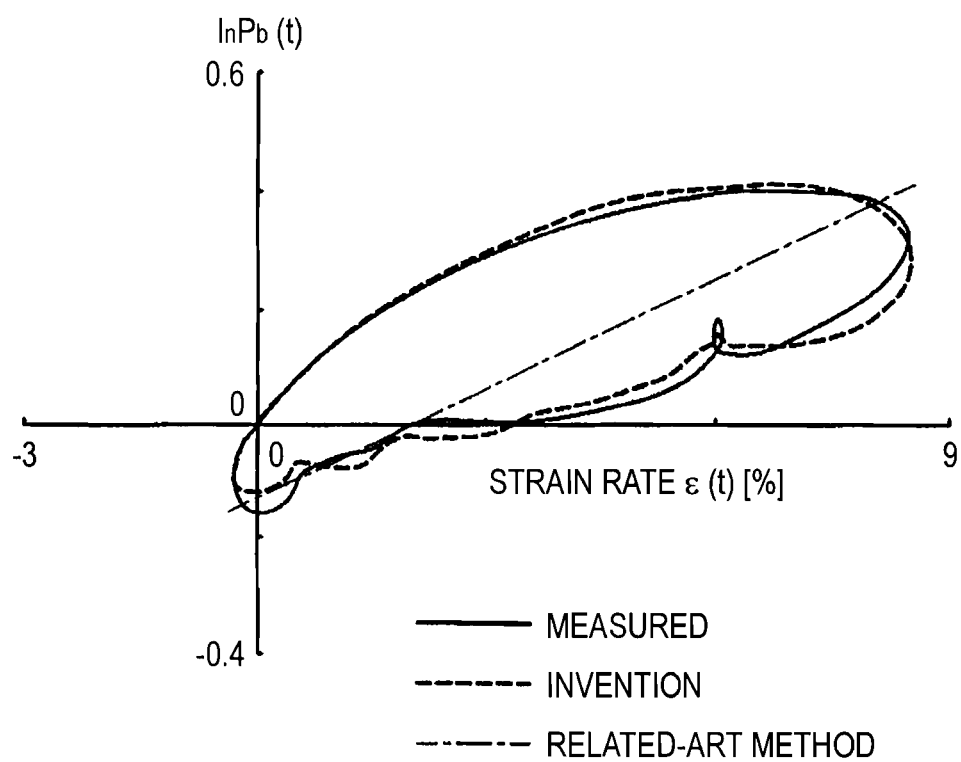
FIG. 8 is a view showing that estimated values from mechanical characteristic values obtained in the first embodiment of the vessel wall monitoring apparatus of the invention coincide with measured values.

FIG. 8 shows a comparison of the stiffness $\beta$ which is obtained with respect to a twentysomething subject by the technique of the embodiment, and the stiffness parameter $\beta_{sf}$ obtained by the related-art technique. In the figure, the abscissa indicates strain $\epsilon$, the ordinate indicates the log-linearization blood pressure, and measured and estimated waveforms are drawn. It is clearly shown that the curve (thin broken line) according to the embodiment of the invention is well coincident with the measured waveform (solid line) showing hysteresis. By contrast, it is seen that the stiffness parameter (long broken line) obtained by the related-art technique is linear, and cannot show hysteresis. The coefficient of determination in the embodiment of the invention is 0.98, and by contrast that in the related-art technique is 0.576. It is clear that the embodiment of the invention shows an excellent degree of coincidence.

Figure 9:
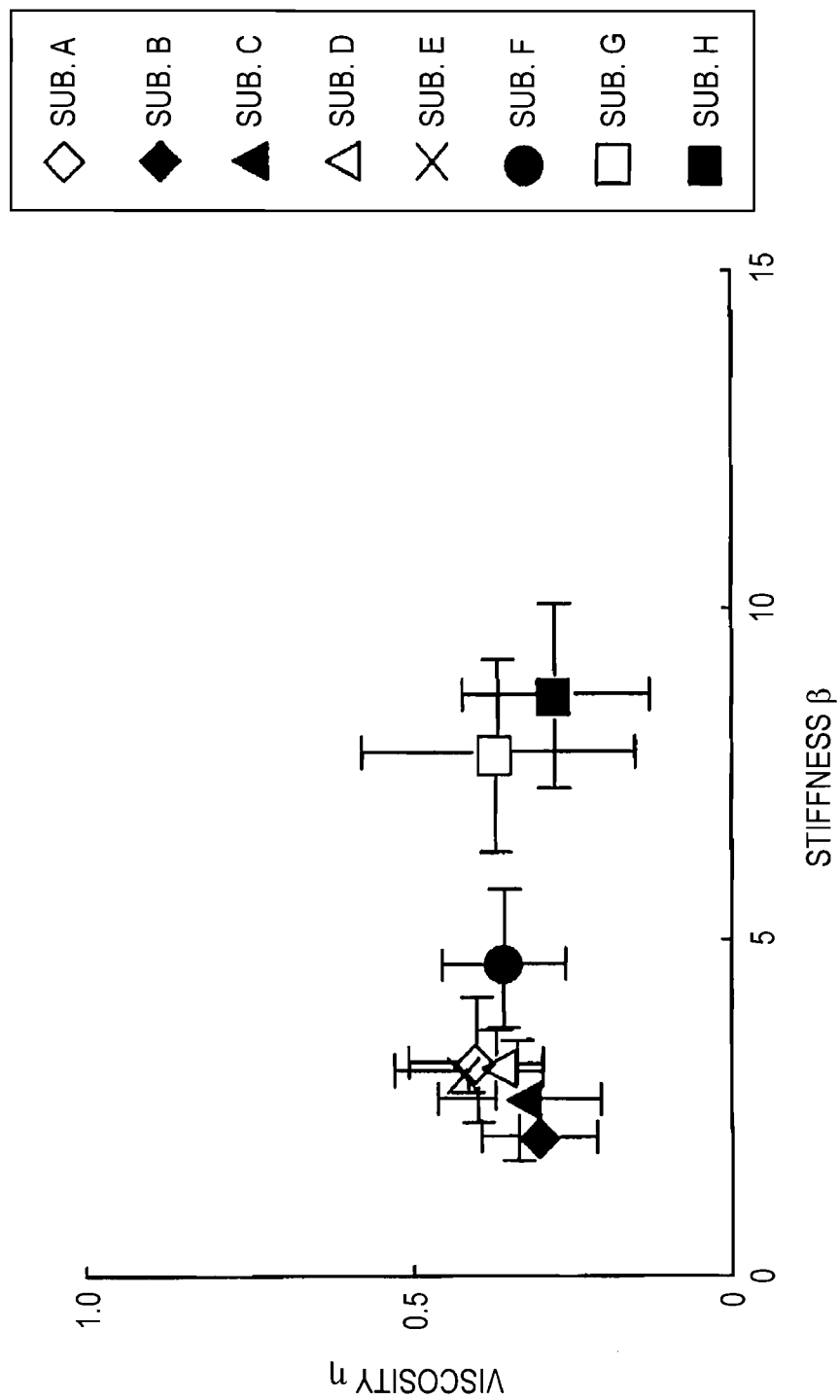
FIG. 9 is a view showing that the stiffness and the viscosity are parameters which are independent from mechanical characteristic values obtained in the first embodiment of the vessel wall monitoring apparatus of the invention.

FIG. 9 shows relationships between $\beta$ and $\eta$ which are obtained from eight subjects indicated by Sub. A to Sub. H. In FIG. 9, it is seen that a result in which plots of the eight subjects are arranged along a straight line or a curve, and which may recall relevance does not appear, and $\beta$ and $\eta$ have information which is entirely independent. Therefore, it is understood that there is a possibility that, when the viscosity $\eta$ is obtained, arteriosclerosis can be evaluated in more detail as compared with the related-art method.

Figure 10:
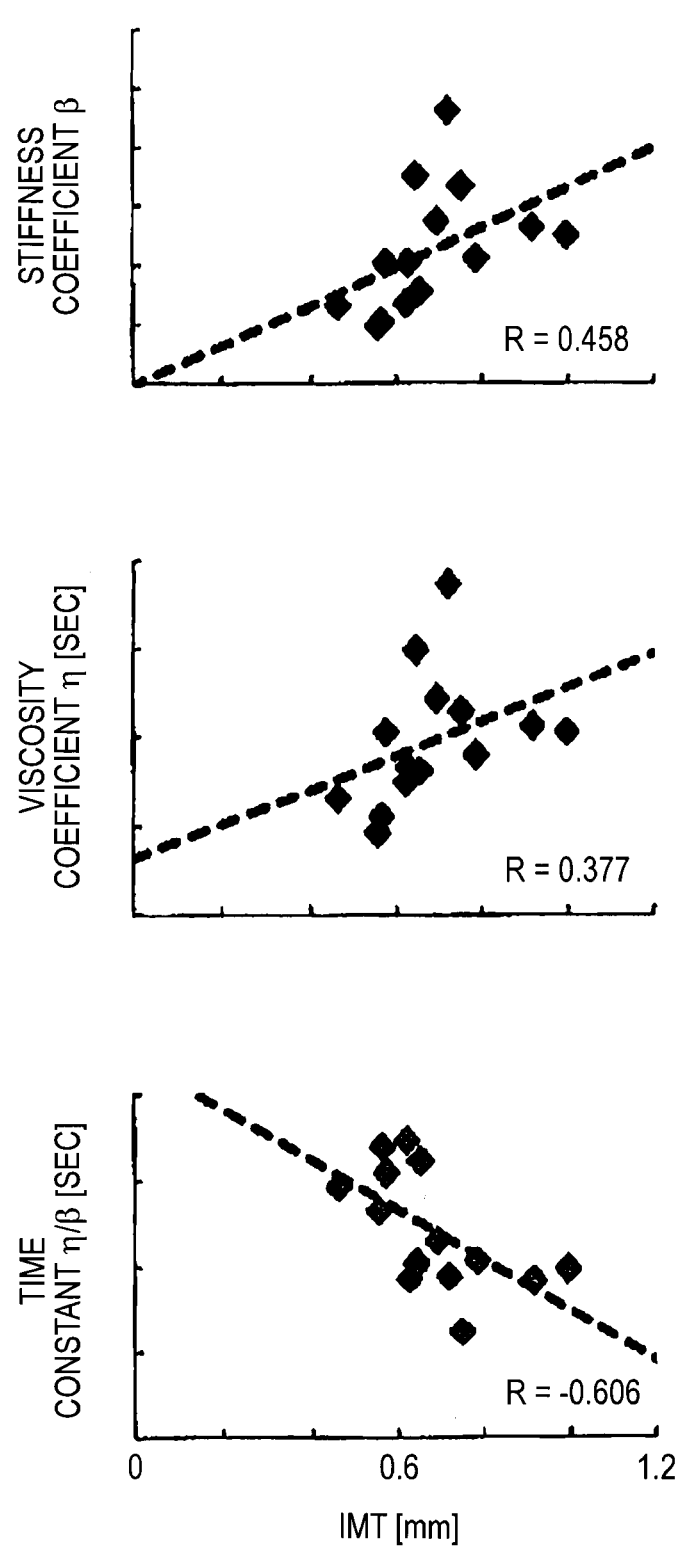
FIG. 10 is a view showing relationships between a time constant and the carotid artery intima-media complex thickness which are obtained in the first embodiment of the vessel wall monitoring apparatus of the invention.

FIG. 10 shows relationships between the carotid artery intima-media complex thickness (hereinafter, referred to as IMT) which was measured with respect to fourteen subjects, and $\beta$, $\eta$, and $\eta/\beta$. The ratio $\eta/\beta$ is called the time constant. The term IMT indicates the thickness of the artery vessel wall, and the thickness increases with age. It is said that, in the case of having a risk factor for arteriosclerosis, the thickness increase advances. From FIG. 10, it is seen that $\eta/\beta$ is most correlated with the IMT. This means that the simultaneous acquisition of $\beta$ and $\eta$ is useful.

In order to obtain the time constant $\eta/\beta$, from the obtained stiffness $\beta$ and viscosity $\eta$, the regression calculating unit 26 may calculate the ratio of the stiffness $\beta$ and the viscosity $\eta$. The time constant $\eta/\beta$ which is calculated by the regression calculating unit 26 is subjected to an outputting process such as that the output is caused by the display controlling unit 27 to be displayed together with or separately from the stiffness $\beta$, the viscosity $\eta$, and the inertia $\mu$ on the displaying portion 8. The time constant $\eta/\beta$ is one form of the ratio of the stiffness $\beta$ and the viscosity $\eta$.

Second Embodiment

An ultrasonic diagnostic apparatus for measuring r(t) which is the vessel radius is expensive, and requires skills. Therefore, a method of determining $\beta$, $\eta$, and $\mu$ based on a plethysmogram of blood in a vessel will be described. First, the principle of determining r(t) based on a plethysmogram will be described in detail.

(Plethysmogram)

Pulse waves includes a pressure pulse wave in which blood pressure variations in a vessel are recorded, and a volume pulse wave in which changes of the volume of the blood are recorded. The term "plethysmogram" in the specification corresponds to the volume pulse wave.

Figure 11:
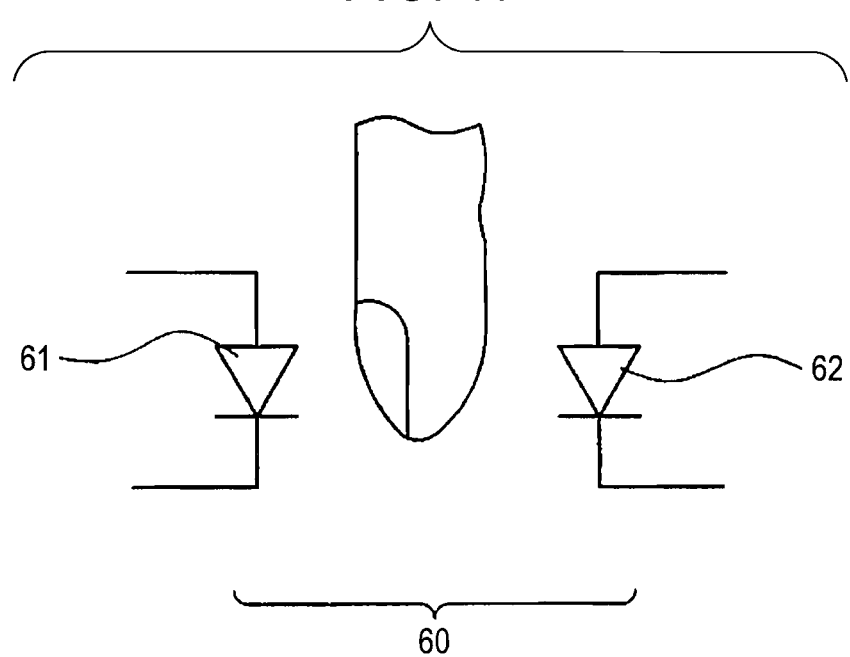
FIG. 11 is a view showing the configuration of a part of a second embodiment of the vessel wall monitoring apparatus of the invention.

Hereinafter, a method of detecting a plethysmogram of a vessel will be described. In the detection, a photoplethysmogram 60 such as shown in FIG. 11 configured by an LED (light emitting diode) 61 and a photodiode 62 is used.

When light emitted from the LED 61 impinges on a finger of the human body, the light is transmitted through the finger and a vessel inside the finger to reach the photodiode 62. In this case, following (Exp. 2) holds in accordance with the Lambert-Beer Law.

$$A_D = \ln(I_0/I_D) = ECD \quad \text{(Exp. 2)}$$

In (Exp. 2) above, D indicates the thickness of the human body, $A_D$ indicates the optical density of the thickness D with respect to the human body, C indicates the concentration of the light absorbing material (a vessel and blood), $I_0$ indicates the transmitted light intensity, $I_D$ indicates the transmitted light intensity, and E indicates the absorption constant of the light absorbing material.

It is assumed that the thickness of the human body is changed from D to D+$\Delta$D(t) by a change of the diameter of a vessel in the human body, and therefore the optical density is A(t) and the transmitted light intensity is $I_D - \Delta I(t)$. Then, the fluctuation component $\Delta A(t)$ of the optical density of a vessel is expressed as (Exp. 3) below.

$$\Delta A(t) = \ln(I_D/(I_D - \Delta I(t))) = EC\Delta D(t) \quad \text{(Exp. 3)}$$

When the fluctuation component $\Delta A(t)$ of the optical density indicated by (Exp. 3) is measured, the measured component corresponds to the above-mentioned plethysmogram $P_1$.

When a change of the vessel diameter in the human body is indicated by $\Delta r$, following (Exp. 4) holds.

$$P_1 = \Delta A(t) = \Delta r(t)/k \quad \text{(Exp. 4)}$$

where k is a proportional constant.

Hereinafter, a method of calculating the mechanical characteristic values of $\mu$ (inertia), $\eta$ (viscosity), and $\beta$ (stiffness) in the case where a vessel is modeled in a mechanical impedance model based on above-described $P_b(t)$ and $P_1(t)$ will be described.

(Method of Calculating Mechanical Characteristic Values)

In the case of an ultrasonic echo, it is possible to measure a vessel diameter which functions as a reference. By contrast, in the case of a plethysmogram, only the change $\Delta r$ is measured. For the purpose of knowing changes of the stiffness, viscosity, and inertia of one subject, however, it is necessarily sufficiently useful to obtain the stiffness $\beta$, viscosity $\eta$, and inertia $\mu$ which are indicated by (Exp. 5) below.

$$dP_b(t) = \beta dP_1(t) + \eta dP_1'(t) + \mu dP_1''(t) \quad \text{(Exp. 5)}$$

where $P_b(t)$: blood pressure,
$dP_b(t) = \ln(P_b(t)) - \ln(P_b(t_0))$,
$dP_1'(t)$: first derivative of $dP_1(t)$, and
$dP_1''(t)$: second derivative of $dP_1(t)$.

Figure 12:
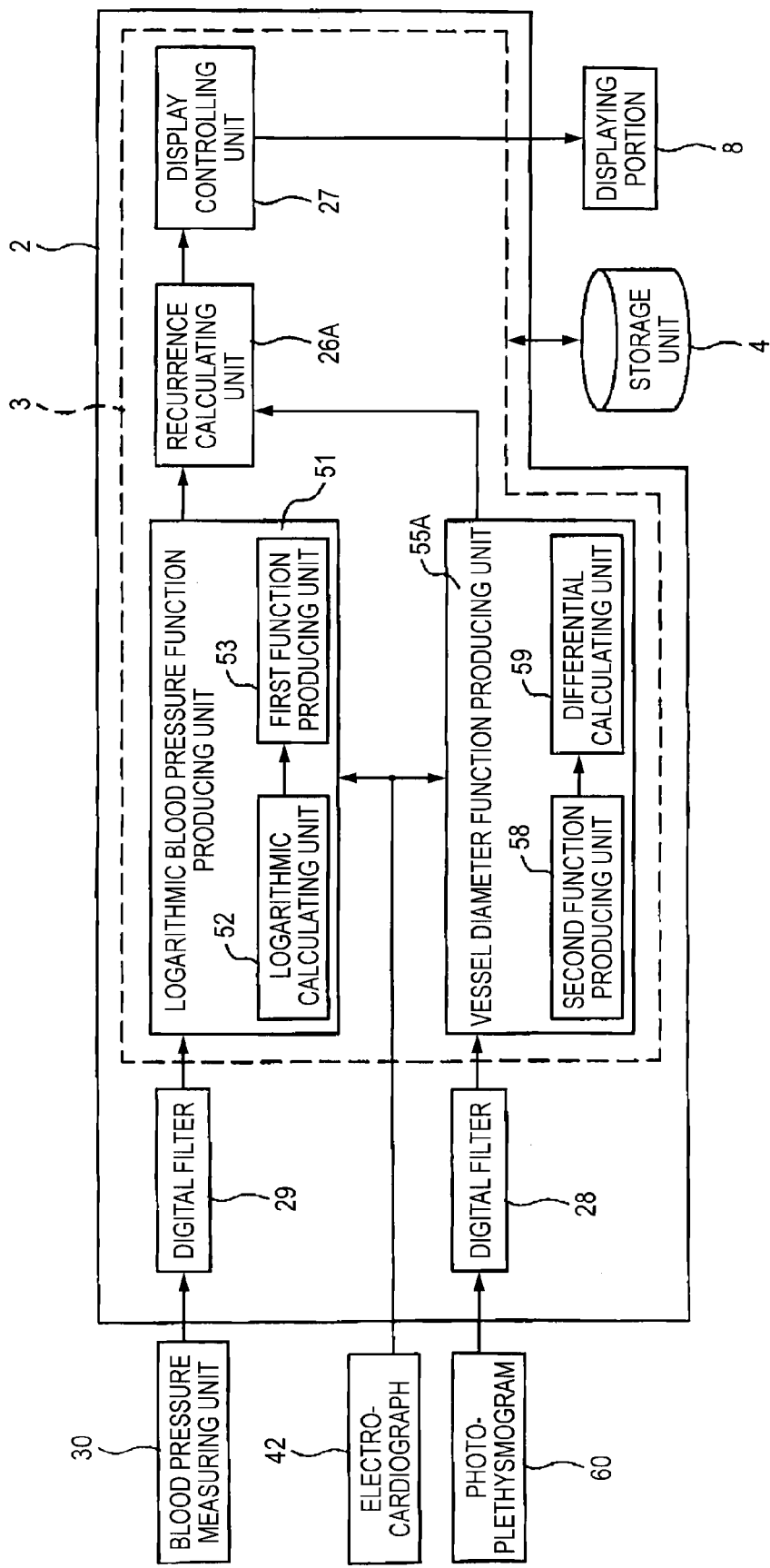
FIG. 12 is a block diagram the configuration of the second embodiment of the vessel wall monitoring apparatus of the invention.
Figure 13:
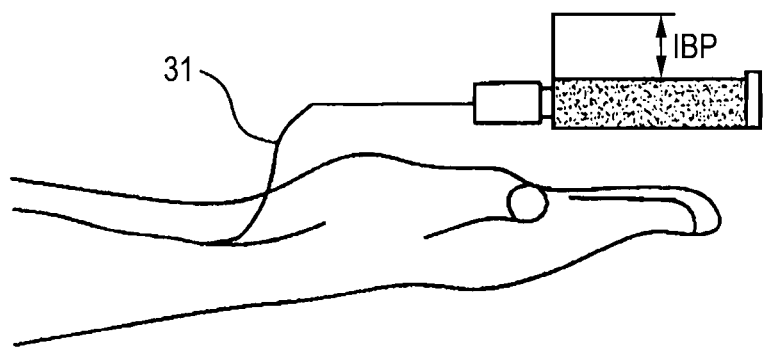
FIG. 13 is a view showing the configuration of a part of the second embodiment of the vessel wall monitoring apparatus of the invention.

FIG. 12 shows the configuration of a vessel wall monitoring apparatus of the second embodiment. The blood pressure is measured by the blood pressure measuring unit 30. Specifically, as shown in FIG. 13, the blood pressure is obtained as the arterial blood pressure IBP which is second biological information, through the catheter 31 inserted into a vessel, measured by a sphygmomanometer which functions as the blood pressure measuring unit 30, and sent as a blood pressure value to the computer system 2. Similarly with the first embodiment, alternatively, the blood pressure measurement may be performed by using another noninvasive measurement method such as the tonometry method.

An electric signal for an electrocardiogram which is obtained through the electrodes 41 is sent to the electrocardiograph 42 to be formed as an electrocardiographic signal which has undergone noise rejection and the like. The electrocardiographic signal is sent to the computer system 2. Moreover, a signal (digital) of the transmitted light intensity which is obtained by the above-described photoplethysmogram 60 is sent to the computer system 2.

The signal of the transmitted light intensity is subjected to noise rejection by the digital filter 28, and then sent to a vessel diameter function producing unit 55A. The vessel diameter function producing unit 55A includes a second function producing unit 58 and a differential calculating unit 59.

Based on data of the transmitted light intensity which are sent from the digital filter 28, the second function producing unit 58 measures the fluctuation component $\Delta A(t)$ of the optical density by using (Exp. 3) above, and sets it as the plethysmogram $P_1$. In the case where the reference appearance timing is indicated by $t_0$, the time period from the reference appearance timing to the next reference appearance timing is indicated by t, and the plethysmogram at t is indicated by $P_1(t)$, the second function producing unit 58 calculates $dP_1(t)=(P_1(t)-P_1(t_0))$. The result of the calculation is sent to the differential calculating unit 59.

The differential calculating unit 59 calculates the first derivative $dP_1'(t)$ of $P_1(t)$ and the second derivative $dP_1''(t)$ of $P_1(t)$, and $dP_1(t)$, $dP_1'(t)$, and $dP_1''(t)$ are sent to a regression calculating unit 26A.

By contrast, the blood pressure value which is output from the blood pressure measuring unit 30 is subjected to noise rejection by the digital filter 29, and then sent to the logarithmic blood pressure function producing unit 51. The process in the logarithmic blood pressure function producing unit 51 is similar to that in the first embodiment. Namely, $dP_b(t)=\ln(P_b(t))-\ln(P_b(t_0))$ is produced, and then sent to the regression calculating unit 26A which is a mechanical characteristic calculating and outputting unit.

The electrocardiographic signal is given from the electrocardiograph 42 to the logarithmic blood pressure function producing unit 51 and the vessel diameter function producing unit 55A. Also the configuration for obtaining the reference appearance timing is similar to that in the first embodiment, and the logarithmic blood pressure function producing unit 51 and the vessel diameter function producing unit 55A can synchronously fetch data.

The regression calculating unit 26A obtains the following functions from the logarithmic blood pressure function producing unit 51 and the vessel diameter function producing unit 55A:

$$dP_b(t)=\ln(P_b(t))-\ln(P_b(t_0)),$$

$dP_1(t)$, $dP_1'(t)$, and $dP_1''(t)$.

When the stiffness $\beta$, the viscosity $\eta$, and the inertia $\mu$ are used, while $dP_b(t)$, $dP_1(t)$, $dP_1'(t)$, and $dP_1''(t)$ above are set as samples, therefore, the regression calculating unit 26A produces (Exp. 5) which is the above-described impedance model expression, and the stiffness $\beta$, the viscosity $\eta$, and the inertia $\mu$ are obtained by a recurrent calculation.

Specifically, the arterial blood pressure and plethysmogram at time t for one heart beat are substituted into the impedance model expression above, and fitting based on the least squares method is performed, whereby the stiffness $\beta$, the viscosity $\eta$, and the inertia $\mu$ are estimated from continuous data for one heart beat. The output of the regression calculating unit 26A is subjected to an outputting process such as that the output is caused by the display controlling unit 27 to be displayed on the displaying portion 8.

Also in the embodiment, the regression calculating unit 26A may detect the time difference $\tau$ between the appearance timing of an inflection point in $dP_b(t)$ above, and that of an inflection point in $dP_1(t)$ above or $\epsilon(t)$, correct $dP_b(t)$ above to $dP_b(t-\tau)$, and correct $dP_b(t_0)$ above to $dP_b(t_0-\tau)$.

Also in the case of a plethysmogram, similarly with the vessel diameter model, the inertia $\mu$ in a vessel wall is very small, and practically there is a case where, even when vessel mechanical characteristics are expressed by using only the stiffness $\beta$ and the viscosity $\mu$, any practical problem does not arise.

In the above-described configuration, a plethysmogram is obtained by the photoplethysmogram 60. Alternatively, a plethysmogram may be obtained by using a strain gauge in place of the photoplethysmogram 60. In the case where a plethysmogram is obtained by using a strain gauge, a change of the circumferential length of a part of the human body such as an arm is measured.

The circumferential length is indicated by L, a change of the circumferential length is indicated by $\Delta L$, it is assumed that the measurement portion has a circular section, and the diameter is indicated by D.

$$L=\pi D$$

When the diameter of the human body is changed by $\Delta D$ as result of a change of the diameter of a vessel included in the human body, $L+\Delta L=\pi(D+\Delta D)$, i.e., $\Delta L=\pi \Delta D$ holds. Similarly with the case of the photoplethysmogram, it is considered that a change in the strain gauge shows a change of the vessel diameter.

Figure 14A:
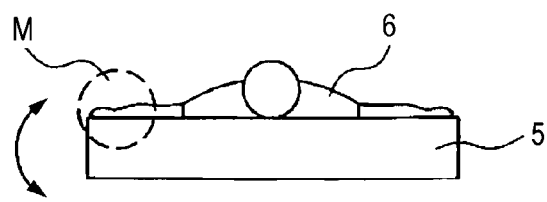
FIGS. 14A, 14B and 14C are views showing steps of an experiment showing an advantage of mechanical characteristic values obtained in the second embodiment of the vessel wall monitoring apparatus of the invention.
Figure 14B:
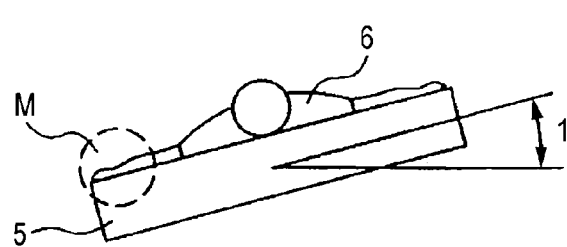
Figure 14C:
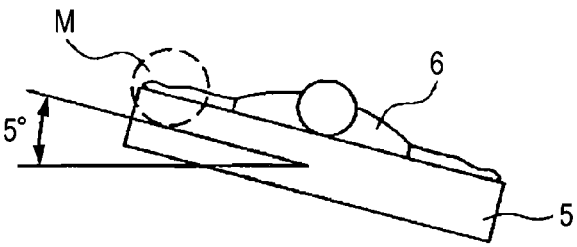

The advantage of the effect of suppressing the blood pressure-dependent properties in the second embodiment using a plethysmogram will be described. FIGS. 14A to 14C show an experimental method. In a state where a subject 6 lies on a bed 5 or the like in the supine position, for example, measurement was performed while inclining the bed as viewed from the head side from a horizontal state as shown in FIG. 14A to the state where the bed is inclined by 10 to 15 degrees to the left or the right as shown in FIG. 14B or FIG. 14C. In this case, the measurement portion by the photoplethysmogram 60 was a hand (measurement portion M), and a technique in which the blood pressure of the hand is made variable by changing the angle of the body by 10 to 15 degrees was employed.

Figure 15:
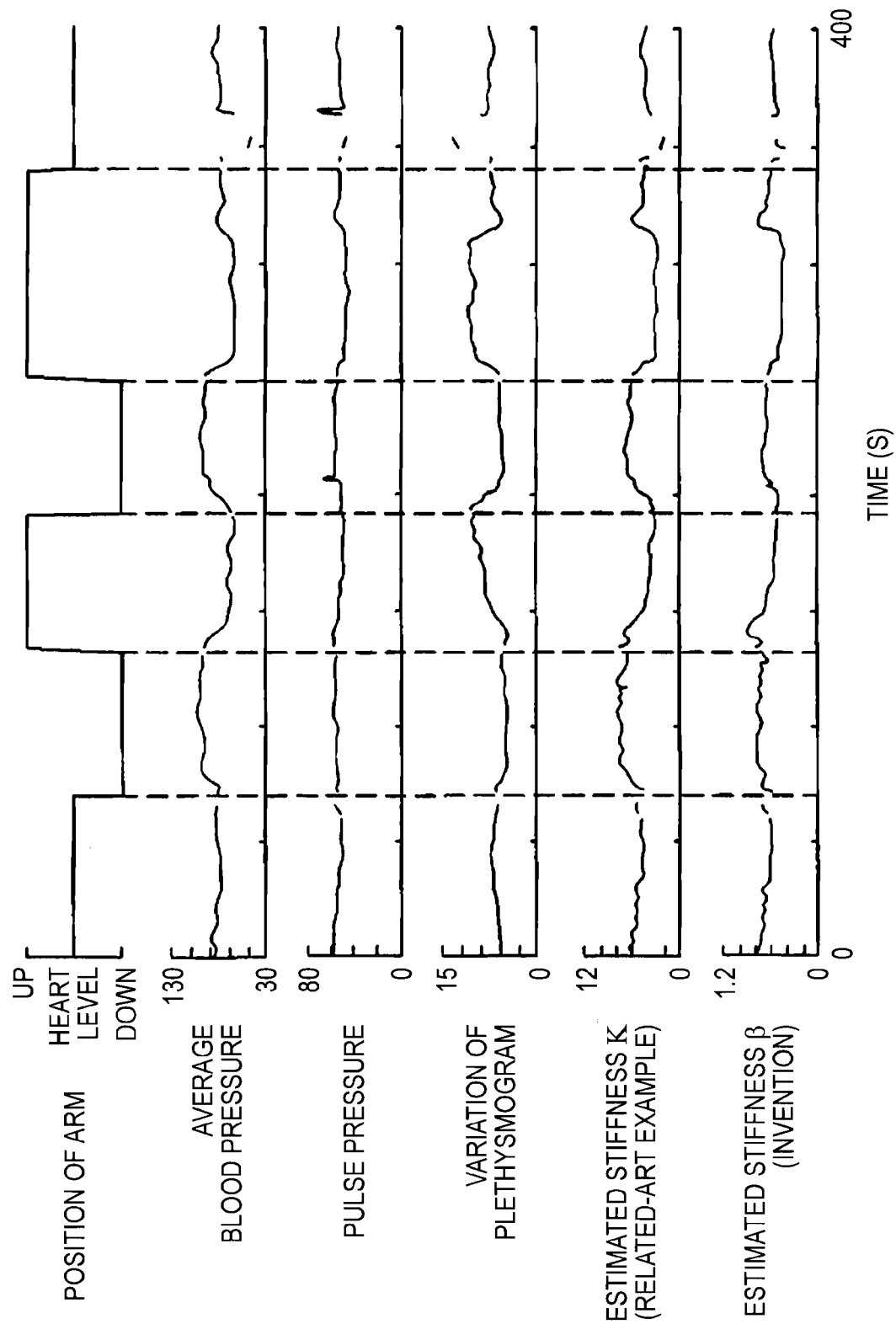
FIG. 15 is a waveform showing a result of the experiment showing the advantage of mechanical characteristic values obtained in the second embodiment of the vessel wall monitoring apparatus of the invention.

A result of the experiment is shown in FIG. 15. The position of the arm is shown in the uppermost portion. In the experiment, as shown in FIGS. 14A to 14C, the left hand is the measurement portion M. Therefore, the state of FIG. 14C is indicated as Up, and that of FIG. 14B is indicated as Down. The waveform which is next to the uppermost portion indicates the mean blood pressure, the next waveform indicates the pulse pressure, and the further next waveform indicates the variation of the plethysmogram. The lowest portion shows the stiffness $\beta$ which is obtained from the log-linearization blood pressure by the embodiment of the invention, and the portion which is above the lowest portion shows the stiffness K which is obtained from a non-logarithmic blood pressure by the related-art method. When comparing the stiffness $\beta$ which is shown in the lowest portion, and which is obtained by the embodiment of the invention, with the stiffness K which is obtained by the related-art method, it is seen that the stiffness $\beta$ in the embodiment of the invention is not largely changed regardless of a change of the body position after the initiation of the operation of changing the angle of the body by 10 to 15 degrees, and influences of the body position change and the blood pressure change due thereto are suppressed.

Figure 16:
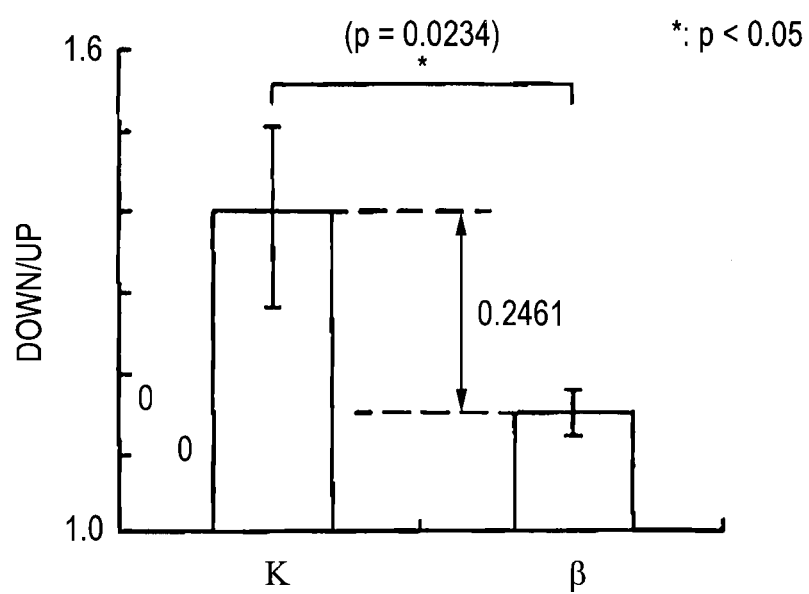
FIG. 16 is a view showing a comparison result obtained from a result of an experiment showing the advantage of mechanical characteristic values obtained in the second embodiment of the vessel wall monitoring apparatus of the invention.

FIG. 16 shows a result of a comparison in which the rate of change of the stiffness due to the body position is compared with respect to four subjects. The following process was performed on values of K and $\beta$ of four subjects. The values of K and $\beta$ are normalized by an average value of a period of 50 seconds in a resting state (the operation of changing the angle of the body by 10 to 15 degrees). The average value and the standard deviation are obtained in Down and Up. Furthermore, the variation rates with respect to Up are obtained in Down and Up. The average value and the standard deviation are obtained from the variation rates of the four subjects. FIG. 16 shows a result of this. A two-sided test at a significance level of 5% was conducted between K and $\beta$ by using a t-test. As a result, it was noted that a significant difference exists at the significance level of 5% between the two models (K and β). It was confirmed that, when the stiffness β in the embodiment of the invention is used, the change is significantly suppressed to a low level.

Also in the second embodiment, in order to obtain the time constant η/β, from the obtained stiffness β and viscosity η, the regression calculating unit 26A may calculate the ratio of the stiffness β and the viscosity η. In this case, the time constant η/β which is calculated by the regression calculating unit 26A is subjected to an outputting process such as that the output is caused by the display controlling unit 27 to be displayed together with or separately from the stiffness β, the viscosity η, and the inertia μ on the displaying portion 8. The time constant η/β is one form of the ratio of the stiffness β and the viscosity η.

According to an aspect of the invention, an impedance model expression is produced by using the logarithmic blood pressure function, the vessel diameter function, and mechanical characteristic values consisting of the stiffness, the viscosity, and the inertia in the case of a mechanical impedance model, at least one of the stiffness, the viscosity, and the inertia is calculated based on the produced impedance model expression and output, and all waveform points obtained from continuous measurements are used. Therefore, the elasticity can be estimated with a higher tolerance to noises and more accurately as compared to the stiffness parameter $\beta_{sf}$ which is obtained from four points of the maximal and minimal blood pressures and the maximum and minimum vessel diameters.

The thus configured invention achieves an effect that, even when the blood pressure of the subject is changed, mechanical characteristics of a vessel can be faithfully estimated. In addition, the hysteresis characteristics of the artery diameter and the vessel internal pressure can be absorbed by the viscosity η, and there is a possibility that the value itself of η can be used in evaluation of vessel mechanical characteristics. Moreover, there is a possibility that, when vessel mechanical characteristics are estimated by using the invention, the artery hardness can be evaluated more accurately and in more detail as compared with the related-art technique. When the ratio of the stiffness and the viscosity is calculated and output, furthermore, the ratio which is a parameter that is highly correlated particularly with the thickness of an artery vessel wall is obtained, and very excellent determination can be performed on arteriosclerosis.

What is claimed is:

1. A vessel wall monitoring apparatus comprising:
   a first detecting unit which detects vessel diameter information based on first biological information obtained from a subject;
   a first producing unit which differentiates the vessel diameter information detected by the first detecting unit, to produce a vessel diameter function;
   a second detecting unit which detects blood pressure based on second biological information obtained from the subject;
   a second producing unit which performs a logarithmic operation on the blood pressure detected by the second detecting unit, to produce a logarithmic blood pressure function; and
   an outputting unit which produces an impedance model expression by using: the vessel diameter function; the logarithmic blood pressure function; and mechanical characteristic values including a stiffness, viscosity, and inertia in a mechanical impedance model of a vessel wall, and which calculates and outputs at least one of a stiffness, viscosity, and inertia of a vessel wall of the subject based on the produced impedance model expression.

2. The vessel wall monitoring apparatus according to claim 1, wherein the first detecting unit detects the vessel diameter information based on the first biological information obtained by an ultrasonic diagnostic apparatus using an ultrasonic echo.

3. The vessel wall monitoring apparatus according to claim 1, wherein
   the vessel diameter information includes a plethysmogram, and
   the first detecting unit detects the plethysmogram based on the first biological information obtained by a photoelectric sensor or a strain gauge.

4. The vessel wall monitoring apparatus according to claim 1, wherein
   the first producing unit uses the vessel diameter information detected by the first detecting unit based on the first biological information obtained at a reference appearance timing and a next reference appearance timing of a blood pressure waveform,
   the second producing unit uses the blood pressure detected by the second detecting unit based on the second biological information obtained at the reference appearance timing and the next reference appearance timing of the blood pressure waveform, and
   each of the reference appearance timing and the next reference appearance timing is obtained from an inflection point of the blood pressure waveform.

5. The vessel wall monitoring apparatus according to claim 4, wherein the logarithmic blood pressure function includes $$dP_b(t)=\ln(P_b(t))-\ln(P_b(t_0)), \text{ and}$$

the vessel diameter function includes:

$$\epsilon(t)=(r(t)-r(t_0))/r(t_0);$$

$\epsilon'(t)$ which is a first derivative of $\epsilon(t)$; and
$\epsilon''(t)$ which is a second derivative of $\epsilon(t)$,
where $t_0$ indicates the reference appearance timing, t indicates a time period from the reference appearance timing to the next reference appearance timing, $P_b(t)$ indicates a blood pressure value at t, and r(t) indicates a vessel diameter at t, and
the impedance model expression includes
$dP_b(t)=\ln(P_b(t))-\ln(P_b(t_0))=\beta\epsilon(t)+\eta\epsilon'(t)+\mu\epsilon''(t)$, where β indicates the stiffness, η indicates the viscosity, and μ indicates the inertia, on which a recurrent calculation is performed to output the at least one of the stiffness, the viscosity, and the inertia.

6. The vessel wall monitoring apparatus according to claim 5, wherein the outputting unit detects a time difference τ between an appearance timing of the inflection point in $dP_b(t)$ and an appearance timing of the inflection point in $\epsilon(t)$, and the outputting unit corrects $dP_b(t)$ to $dP_b(t-\tau)$ and corrects $dP_b(t_0)$ to $dP_b(t_0-\tau)$.

7. The vessel wall monitoring apparatus according to claim 4, wherein the logarithmic blood pressure function includes $$dP_b(t)=\ln(P_b(t))-\ln(P_b(t_0)), \text{ and}$$

the vessel diameter function includes:

$$dP_1(t)=(P_1(t)-P_1(t_0));$$

$dP_1'(t)$ which is a first derivative of $P_1(t)$; and
$dP_1''(t)$ which is a second derivative of $P_1(t)$,
where $t_0$ indicates the reference appearance timing, t indicates a time period from the reference appearance timing to the next reference appearance timing, $P_b(t)$ indicates a blood pressure value at t, and $P_1(t)$ indicates a plethysmogram at t, and the impedance model expression includes $dP_b(t)=\ln(P_b(t))-\ln(P_b(t_0))=\beta dP_1(t)+\eta dP_1'(t)+\mu dP_1''(t)$,
where $\beta$ indicates the stiffness, $\eta$ indicates the viscosity, and $\mu$ indicates the inertia, on which a recurrent calculation is performed to output the at least one of the stiffness, the viscosity, and the inertia.

8. The vessel wall monitoring apparatus according to claim 7, wherein
the outputting unit detects a time difference $\tau$ between an appearance timing of the inflection point in $dP_b(t)$ and an appearance timing of the inflection point in $dP_b(t)$, and
the outputting unit corrects $dP_b(t)$ to $dP_b(t-\tau)$ and corrects $dP_b(t_0)$ to $dP_b(t_0-\tau)$.

9. The vessel wall monitoring apparatus according to claim 1, wherein
the first producing unit uses the vessel diameter information detected by the first detecting unit based on the second biological information obtained at a reference appearance timing and a next reference appearance timing of a blood pressure waveform,
the second producing unit uses the blood pressure detected by the second detecting unit based on the second biological information obtained at the reference appearance timing and the next reference appearance timing of the blood pressure waveform, and
each of the reference appearance timing and the next reference appearance timing is obtained from an R-wave of an electrocardiogram.

10. The vessel wall monitoring apparatus according to claim 9, wherein the logarithmic blood pressure function includes $dP_b(t)=\ln(P_b(t))-\ln(P_b(t_0))$, and the vessel diameter function includes:

$\epsilon(t)=(r(t)-r(t_0))/r(t_0)$;

$\epsilon'(t)$ which is a first derivative of $\epsilon(t)$; and
$\epsilon''(t)$ which is a second derivative of $\epsilon(t)$,
where $t_0$ indicates the reference appearance timing, t indicates a time period from the reference appearance timing to the next reference appearance timing, $P_b(t)$ indicates a blood pressure value at t, and $r(t)$ indicates a vessel diameter at t, and
the impedance model expression includes $dP_b(t)=\ln(P_b(t))-\ln(P_b(t_0))=\beta\epsilon(t)\eta\epsilon'(t)+\mu\epsilon''(t)$, where $\epsilon$ indicates the stiffness, $\eta$ indicates the viscosity, and $\mu$ indicates the inertia, on which a recurrent calculation is performed to output the at least one of the stiffness, the viscosity, and the inertia.

11. The vessel wall monitoring apparatus according to claim 10, wherein
the outputting unit detects a time difference $\tau$ between an appearance timing of an inflection point of the blood pressure waveform in $dP_b(t)$ and an appearance timing of the inflection point of the blood pressure waveform in $\epsilon(t)$, and the outputting unit corrects $dP_b(t)$ to $dP_b(t-\tau)$ and corrects $dP_b(t_0)$ to $dP_b(t_0-\tau)$.

12. The vessel wall monitoring apparatus according to claim 9, wherein the logarithmic blood pressure function includes $dP_b(t)=\ln(P_b(t))-\ln(P_b(t_0))$, and the vessel diameter function includes:

$dP_1(t)=(P_1(t)-P_1(t_0))$;

$dP_1'(t)$ which is a first derivative of $P_1(t)$; and
$dP_1''(t)$ which is a second derivative of $P_1(t)$,
where $t_0$ indicates the reference appearance timing, t indicates a time period from the reference appearance timing to the next reference appearance timing, $P_b(t)$ indicates a blood pressure value at t, and $P_1(t)$ indicates a plethysmogram at t, and
the impedance model expression includes $dP_b(t)=\ln(P_b(t_0))-\ln(P_b(t_0))=\beta dP_1(t)+\eta dP_1'(t)+\mu dP_1''(t)$,
where $\beta$ indicates the stiffness, $\eta$ indicates the viscosity, and $\mu$ indicates the inertia, on which a recurrent calculation is performed to output the at least one of the stiffness, the viscosity, and the inertia.

13. The vessel wall monitoring apparatus according to claim 12, wherein the outputting unit detects a time difference $\tau$ between an appearance timing of an inflection point of the blood pressure waveform in $dP_b(t)$ and an appearance timing of the inflection point of the blood pressure waveform in $dP_1(t)$, and
the outputting unit corrects $dP_b(t)$ to $dP_b(t-\tau)$ and corrects $dP_b(t_0)$ to $dP_b(t_0-\tau)$.

14. The vessel wall monitoring apparatus according to claim 1, wherein the outputting unit calculates the stiffness and the viscosity and calculates and outputs a ratio of the stiffness and the viscosity.

* * * * *